United States Patent
Dupelle et al.

(10) Patent No.: US 8,577,462 B2
(45) Date of Patent: Nov. 5, 2013

(54) CONDITION SENSOR FOR MEDICAL DEVICE PACKAGE

(75) Inventors: Michael R. Dupelle, N. Attleboro, MA (US); Michael Parascandola, Londonderry, NH (US); Marc Cordaro, Sudbury, MA (US); Sheldon S. White, Brookline, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 1305 days.

(21) Appl. No.: 11/481,245

(22) Filed: Jul. 5, 2006

(65) Prior Publication Data

US 2008/0009911 A1  Jan. 10, 2008

(51) Int. Cl.
*A61N 1/00* (2006.01)

(52) U.S. Cl.
USPC ............. 607/36; 607/28; 607/142; 206/210; 206/701

(58) Field of Classification Search
USPC ............ 607/1–2, 4–5, 38, 36, 142; 206/210, 206/701; 361/122, 500, 502–504, 508
See application file for complete search history.

(56) References Cited

U.S. PATENT DOCUMENTS

| | | | |
|---|---|---|---|
| 5,402,884 | A | 4/1995 | Gilman et al. |
| 5,591,213 | A | 1/1997 | Morgan |
| 5,755,742 | A | 5/1998 | Schuelke et al. |
| 5,897,522 | A | 4/1999 | Nitzan |
| 5,984,102 | A | 11/1999 | Tay |
| 6,075,369 | A | 6/2000 | Morgan |
| 6,782,293 | B2 | 8/2004 | Dupelle et al. |
| 2005/0277991 | A1 | 12/2005 | Covey et al. |
| 2006/0178706 | A1 | 8/2006 | Lisogurski et al. |

FOREIGN PATENT DOCUMENTS

WO  97/43000  11/1997

OTHER PUBLICATIONS

Cardiac Science Brochure. The Science of Survival (2002).
Cardiac Science Presentation, the Science of Survival and the Powerheart AED (2003).
Philips Medical Systems Technical Note, Problems Associated with Pre-Attaching Pads to the Heartstart FR and FR2 Series Defibrillators Note (Feb. 2004).
Philips Medical Systems Instructions for Use for Heartstart Onsite M5066A Automated External Defibrillator, Edition 4 (2002).

*Primary Examiner* — Christopher D Koharski
*Assistant Examiner* — Deborah Malamud
(74) *Attorney, Agent, or Firm* — Fish & Richardson P.C.

(57) ABSTRACT

A package in which a medical device is stored, the package comprising an outer shell providing a vapor barrier, a medical device positioned in the interior space inside the outer shell, the medical device including a liquid-containing element that is subject to drying out, a condition sensor comprising two metallic elements and a conductive water-containing element, each of the two metallic elements being composed of different metals, with each of the different metals selected so that the two metallic elements form an anode and a cathode of an electrochemical cell, so that the water-containing element forms the electrolyte of the electrochemical cell, and the voltage of the cell provides an indication the conductive water-containing element of the medical device has dried out.

16 Claims, 12 Drawing Sheets

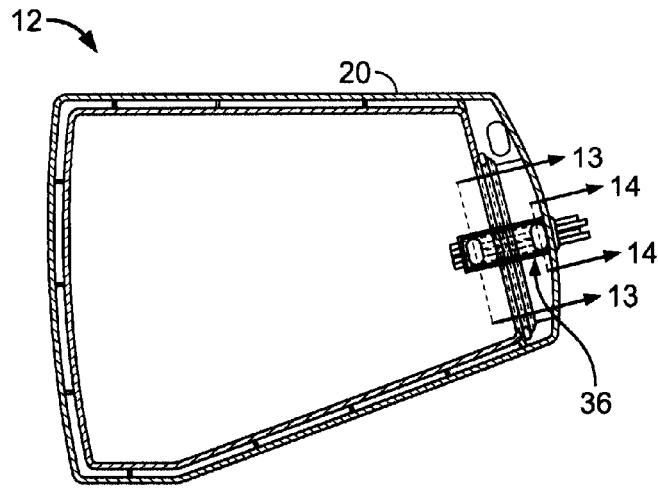
FIG. 12
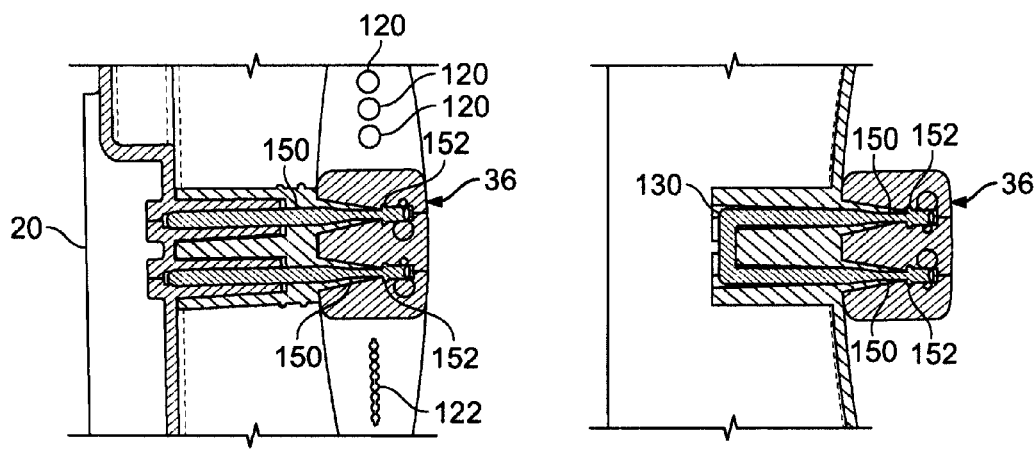
FIG. 13
FIG. 14

CONDITION SENSOR FOR MEDICAL DEVICE PACKAGE

TECHNICAL FIELD

This invention relates to sealed packages for medical devices.

BACKGROUND

There is a growing trend toward the replacement of multiple use defibrillator paddles with single-use disposable therapeutic electrodes for defibrillation, external transthoracic pacing, or the combination of both. This trend is driven by numerous factors including, but not limited to: (1) convenience related to not having to apply a conductive media (e.g., gel), (2) speed of care when switching from delivering a defibrillation shock to a pacing current, (3) caregiver safety in that contact with the patient can be avoided as the therapy can be delivered remotely from the host device, and (4) increased use of defibrillators incorporating algorithms that analyze the presented ECG rhythm for appropriateness of therapeutic (shock) delivery. These applications typically work only with single-use, disposable therapeutic electrodes.

Defibrillation of cardiac arrest is a time sensitive matter. It is well documented that for every minute delivery is delayed, the chance of survival falls 7 to 10 percent. One way manufacturers have addressed the time to shock issue, has been to create electrodes that can be pre-connected to a defibrillator. If electrodes are not pre-connected or present, valuable time will be lost, and chance of survival diminished as responders must address this matter.

Owing to many factors both chemical and environmental in nature, single-use therapeutic electrodes have a finite shelf life. Manufacturers typically label individual electrodes with specific dates of expiration beyond which therapeutic delivery cannot be insured. It is incumbent on the operator to read the electrode labeling prior to use to insure a non-expired electrode is deployed for therapy.

Electrode packaging is designed to be both airtight and watertight. This is to minimize environmental fluctuations that might shorten the useful life of an electrode. Should an electrode package be breached, chemical reactions will be accelerated and shelf life shortened.

Checking for the condition of an electrode package, or reading the expiration date are time consuming are potential points of error that have the potential to adversely affect a defibrillator's therapeutic capabilities.

SUMMARY

In a first aspect, the invention features a package in which a medical device is stored, the package comprising an outer shell providing a vapor barrier between an interior space inside the outer shell and an exterior environment, a medical device positioned in the interior space inside the outer shell, the medical device including a liquid-containing element that is subject to drying out as liquid from the liquid-containing element vaporizes and travels from the interior space to the external environment, a condition sensor comprising two metallic elements, each of the two metallic elements being composed of different metals, with each of the different metals selected so that the two metallic elements form an anode and a cathode of an electrochemical cell, each of the two metallic elements being in electrical contact with a conductive water-containing element, so that the water-containing element forms the electrolyte of the electrochemical cell, and an electrically conductive path extending from each of the metallic elements to a location wherein the electrochemical potential formed between the metallic elements can be measured to provide an indication of the degree to which the conductive water-containing element has dried out.

Preferred implementations of this aspect of the invention may incorporate one or more of the following. The medical device stored in the package may comprise at least one electrode, and wherein the electrode may include a metallic layer in electrical contact with a conductive liquid-containing layer through which electrical current may be delivered to a patient when the electrode has been applied to a patient, the conductive liquid-containing layer may be subject to drying out as liquid from the liquid-containing layer vaporizes and travels from the interior space to the external environment, and wherein the condition sensor may provide an indication of whether the liquid-containing layer has dried out sufficiently that the electrode should not be used. The metallic elements of the condition sensor may be separate from the metallic layer in the electrode. The electrode may comprise a defibrillation electrode. The conductive liquid-containing layer of the electrode may contain water and may comprise an aqueous gel. The aqueous gel may comprise a solid gel. The aqueous gel may comprise a liquid gel. The water-containing element of the condition sensor may comprise an aqueous gel layer. The metallic elements of the condition sensor may be thin metallic layers and the aqueous gel may be a thin gel layer in contact with each of the metallic layers. The thin gel layer may be a different layer from the conductive liquid-containing layer of the defibrillation electrode. The condition sensor may be configured so as to be retained in the package when the defibrillation electrode has been removed from the package. The electrically conductive paths extending from each of the metallic elements may comprise electrical wires extending from the metallic elements at least to the outer shell. The electrochemical potential may be measured inside the package and communicated to the exterior of the package. The invention may further comprise a gasket element at the perimeter of the outer shell, the gasket element may be shaped and positioned so that one surface of the gasket element may be exposed to the interior space within the outer shell and another surface of the gasket element may be exposed to the exterior environment, the electrically conductive paths from the metallic elements of the condition sensor may extend through the gasket element from the interior space to the exterior environment. The gasket element may be configured so that when the package is opened and the defibrillation electrode applied to the patient, the gasket element may be removed from the package which may cause the electrically conductive paths connected to the further electrical element to be broken. The condition sensor may further comprise a resistive element electrically connected between the two metallic elements. The resistance of the resistive element may be variable. The metals used in the metallic elements of the condition sensor may include at least one metal that is the same as the metal used in the defibrillation electrode.

In a second aspect, the invention features a defibrillator for providing a defibrillation pulse to electrodes applied to the chest of a patient, the defibrillator comprising a pair of electrical outputs for delivering the defibrillation pulse to at least one defibrillation electrode, a pair of electrical inputs for measuring the electrical potential of an electrochemical cell formed within a package containing the defibrillation electrode prior to use of the electrode, processing circuitry and associated software for comparing the electrical potential to one or more thresholds to determine whether a gel layer of the defibrillation electrode remains sufficiently moist for the electrode to function.

Preferred implementations of this aspect of the invention may incorporate one or more of the following. The comparison may determine whether the electrical potential is below a threshold. The comparison may determine whether the rate of change of the electrical potential is above a threshold. The processing circuitry and associated software may include the capability to call for delivery of a warning indication to the user based on the outcome of the comparison. At least one threshold may be determined by reading a value stored in a memory device associated with the defibrillation electrode.

Among the many advantages of the invention (some of which may be achieved only in some of its various aspects and implementations) are the following: The condition of a medical device (e.g., a defibrillation electrode) within a sealed package can be determined automatically, thereby increasing the reliability of the equipment that uses the medical device.

Other features and advantages of the invention will be found in the detailed description, drawings, and claims.

DESCRIPTION OF DRAWINGS

FIG. 12 is a plan view showing the rigid shell of the electrode package with its removable lid removed and its contents removed.

FIG. 13 is a partial cross-sectional view taken along section B-B in FIG. 12 showing a cross section through an inner end of the gasket element of the electrode package.

FIG. 14 is a partial cross-sectional view taken along section A-A in FIG. 12 showing a cross section through an outer end of the gasket element of the electrode package.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
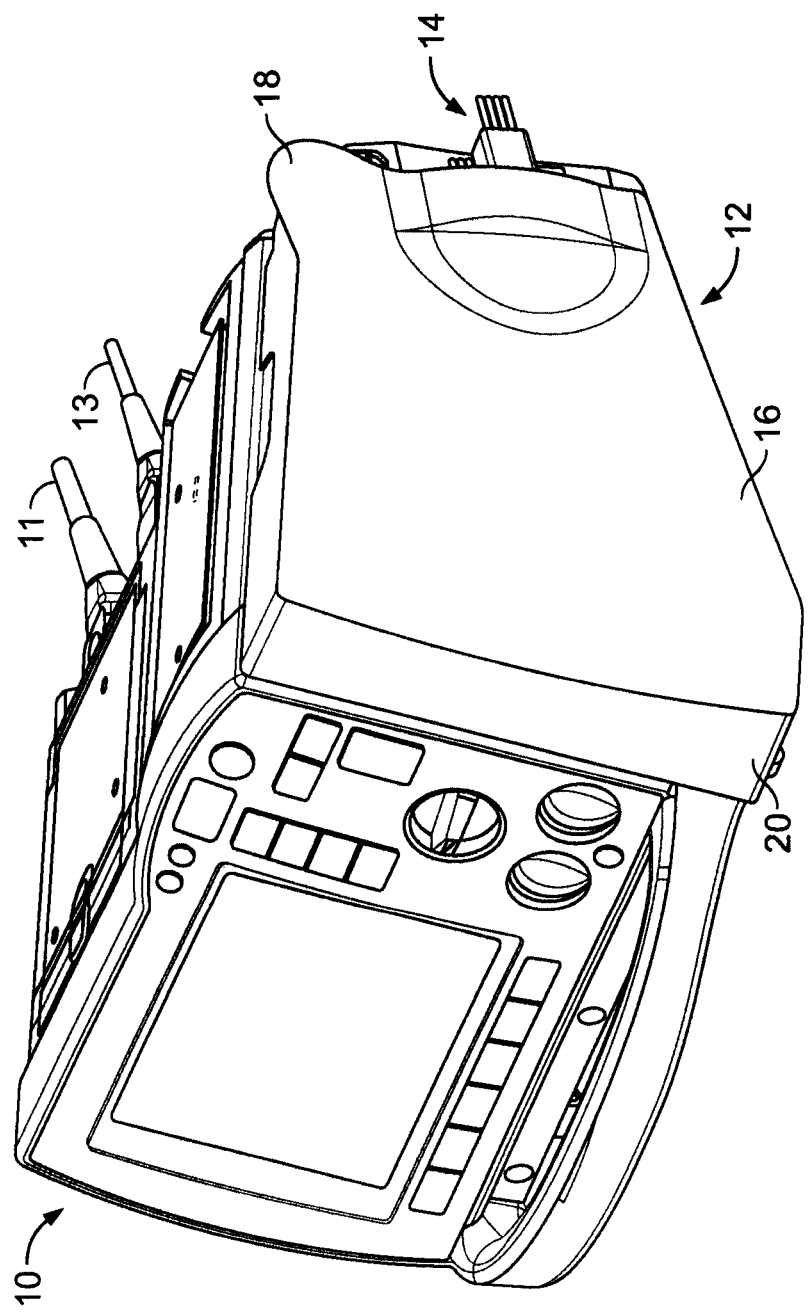
FIG. 1 is a perspective view of a defibrillator implementation of the invention.
Figure 2:
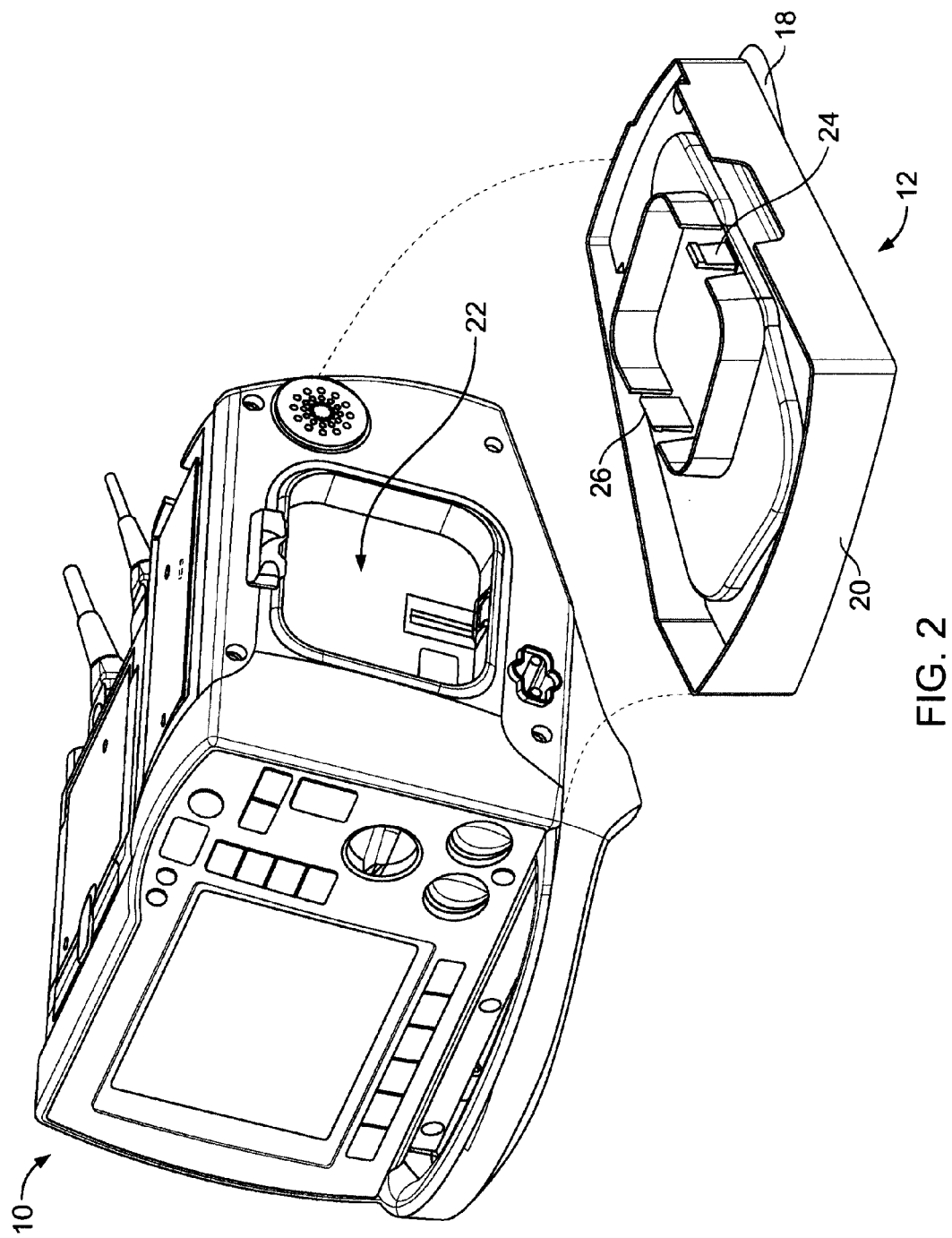
FIG. 2 is a perspective view of the defibrillator of FIG. 1 with an electrode package shown removed.
Figure 4:
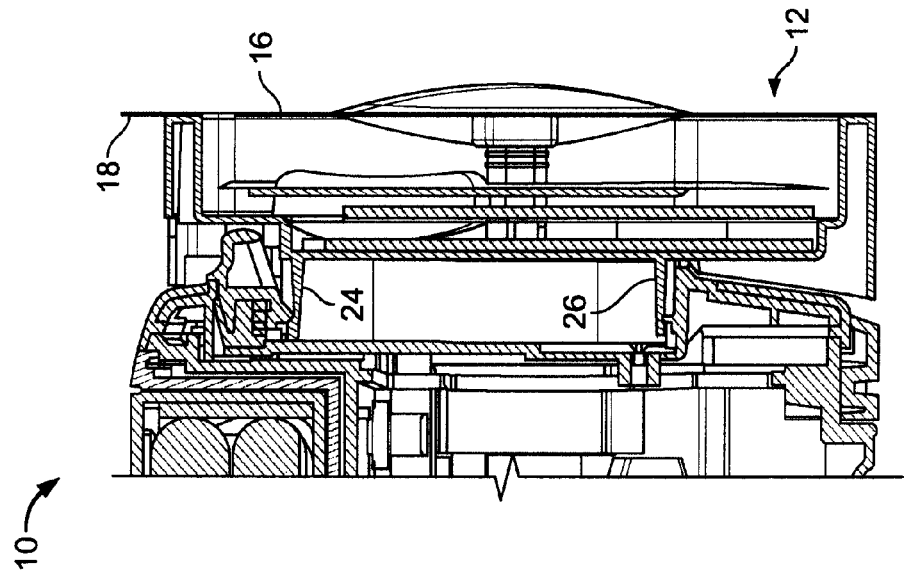
FIG. 4 is a cross-sectional view taken along section 4-4 in FIG. 3.
Figure 3:
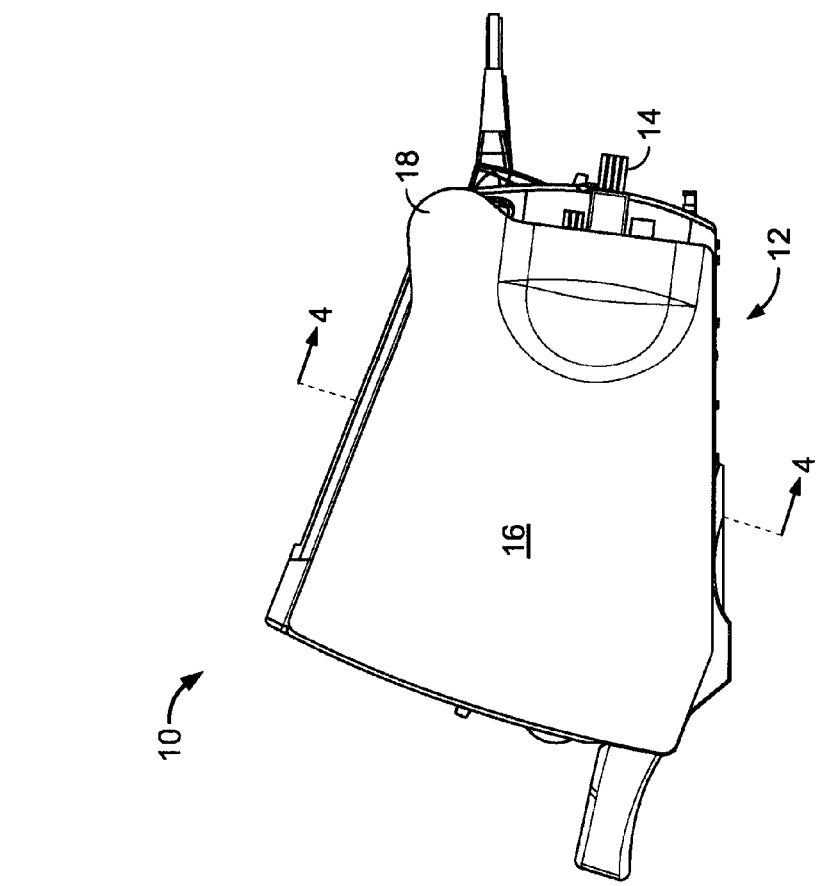
FIG. 3 is a side elevation view of the defibrillator of FIG. 1 looking toward the side with the electrode package.

FIGS. 1-4 show an external defibrillator 10 (e.g., a hospital crash cart defibrillator, such as the R Series manufactured by ZOLL Medical of Chelmsford, Mass.). User interface elements (graphical display, speaker, microphone, input buttons and dials) are provided on the front face of the defibrillator. Attached to the right side of the defibrillator is an electrode package 12, which is removable from the defibrillator, as shown in FIG. 2, and normally electrically connected to the defibrillator by cable 14 even when the defibrillator is not in use. The multi-conductor cable 14 emerging from the electrode package passes through a connector (not shown in FIGS. 1-4, but shown in the schematic of FIG. 11) and divides into two cables 11, 13 which attach to the back of the defibrillator. A removable lid 16 is removed (by grasping tab 18) to open the defibrillator package.

The electrode package 12 includes a rigid base (or tray) 20 (polypropylene), which with the removable lid 16 (foil lined paper) constitutes the outer shell of the package. The base and lid provide a moisture barrier to prevent the gel layers of the electrodes from drying out during the shelf life of the package. The lid is heat sealed to the perimeter of the base (tray). The rigid base (a molded polymer part) is removable snapped into the receptacle 22 on the side of the defibrillator also used to secure a defibrillator paddle. Upper and lower flexible clips 24, 26 snap into engagement with mating elements of the receptacle 22. Engagement of the flexible clips 24, 26 is shown in the cross section of FIG. 4, which shows the electrode package snapped into place on the side of the defibrillator.

Figure 5:
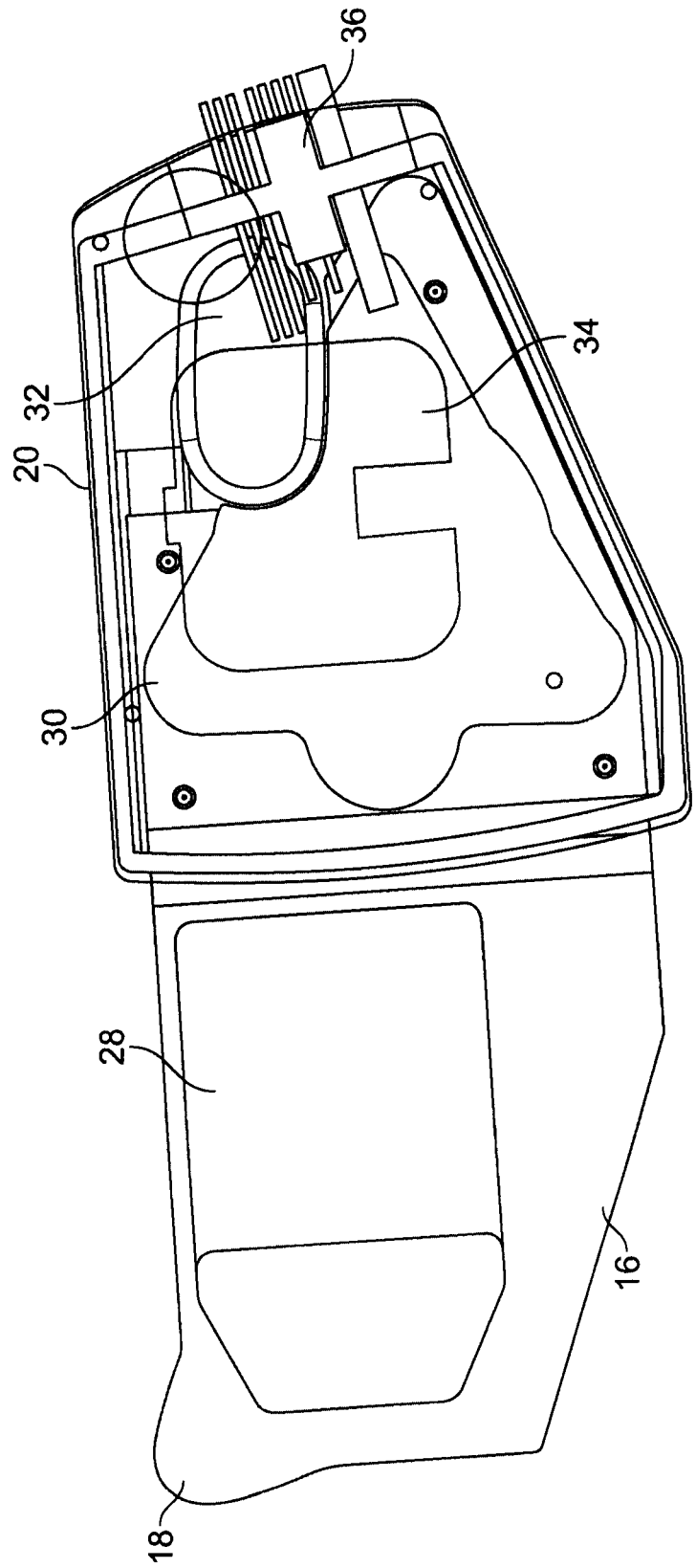
FIG. 5 is a plan view of the electrode package after being opened to expose its contents.

FIG. 5 shows the electrode package with lid 16 peeled back to expose the contents of the package. A first defibrillation electrode 28 (generally square in this plan view) for the back (posterior) of the patient's chest is adhered to a release liner (not shown) secured to the inside face of lid 16. Electrode 28 is peeled off of the release liner and adhered to the back of the chest.

A second defibrillation electrode 30 (generally triangular in this plan view) for the front (anterior) of the patient's chest is adhered to another release liner (not shown) secured to the rigid based of the electrode package. Electrode 30 is an assembly of a defibrillation electrode and three ECG monitoring electrodes, and is described in co-pending U.S. patent application Ser. No. 11/055,572, filed on Feb. 11, 2005, hereby incorporated by reference.

A device for assisting CPR, known as a CPR puck or pad 32, is also stored within the electrode package. A similar CPR pad is described in U.S. Pat. No. 6,782,293, hereby incorporated by reference. It includes an accelerometer for measuring movement of the chest during CPR.

The fourth element within the electrode package is a condition sensor 34 that assists the defibrillator in determining whether the liquid-containing (gel) layers of the defibrillation electrodes are still sufficiently moist to function properly. The condition sensor 34 is not intended to be removed from the package, as it is not used during defibrillation.

Various electrical conductors pass into the electrode package to connect the contents with the defibrillator. These conductors pass through a gasket element 36 that is sealed between the rigid base 20 and removable lid 16 of the package. When the electrodes and CPR puck are removed from the package, the gasket element is also removed, as the electrical conductors for the electrodes and CPR puck extend through the gasket element.

Figure 6:
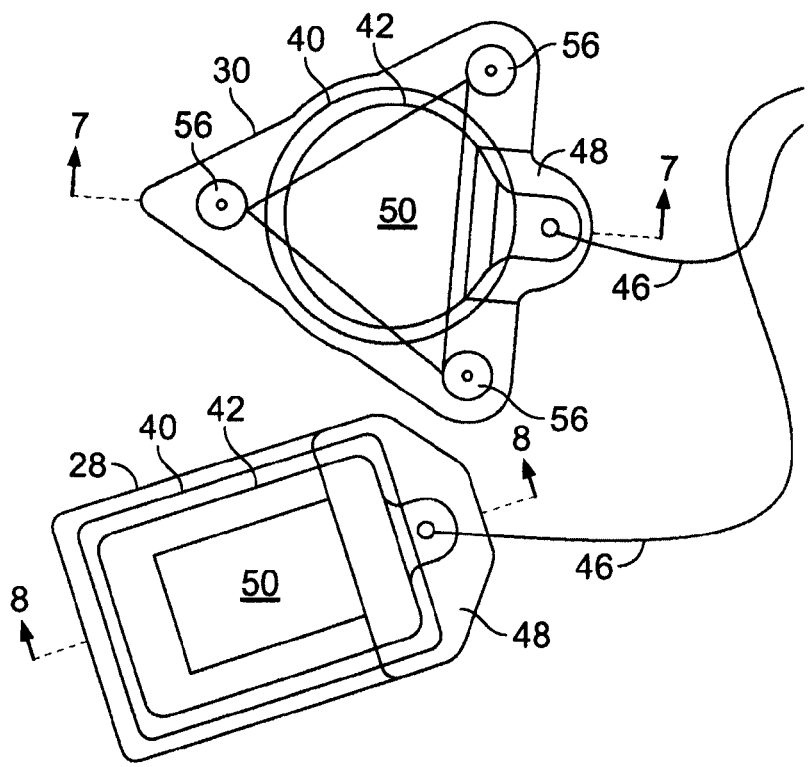
FIG. 6 is a plan view of the two defibrillation electrodes stored inside the electrode package.
Figure 7:
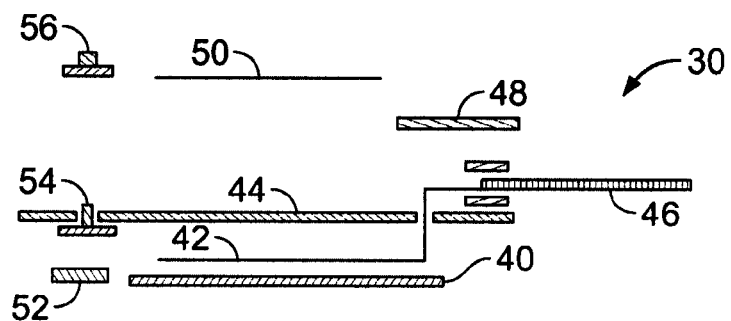
FIG. 7 is an exploded, cross-sectional view taken along 7-7 in FIG. 6.
Figure 8:
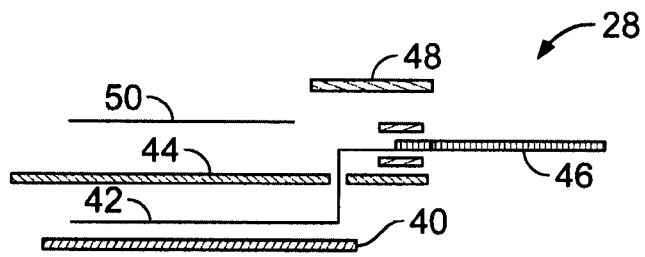
FIG. 8 is an exploded, cross-sectional view taken along 8-8 in FIG. 6.

FIGS. 6-8 show the two defibrillation electrodes 28, 30 in greater detail. The triangular front electrode 30 is shown in FIGS. 6-7. The construction of the electrode is shown in exploded, cross-sectional view in FIG. 7. A conductive liquid-containing layer 40 (solid gel) contacts the patient's skin, and conveys electrical current from the metallic layer 42 (tin plate or other metallic material such as silver chloride) to the patient. The gel and tin layer are supported on foam layer 44, which carries adhesive to secure the electrode to the patient. The metallic layer is connected to wire 46 through which the defibrillation pulse is delivered from the defibrillator. A foam insulator layer 48 covers the area where the metallic layer and wire emerge from the electrode. A label 50 is applied over the foam layer 44.

Figure 21:
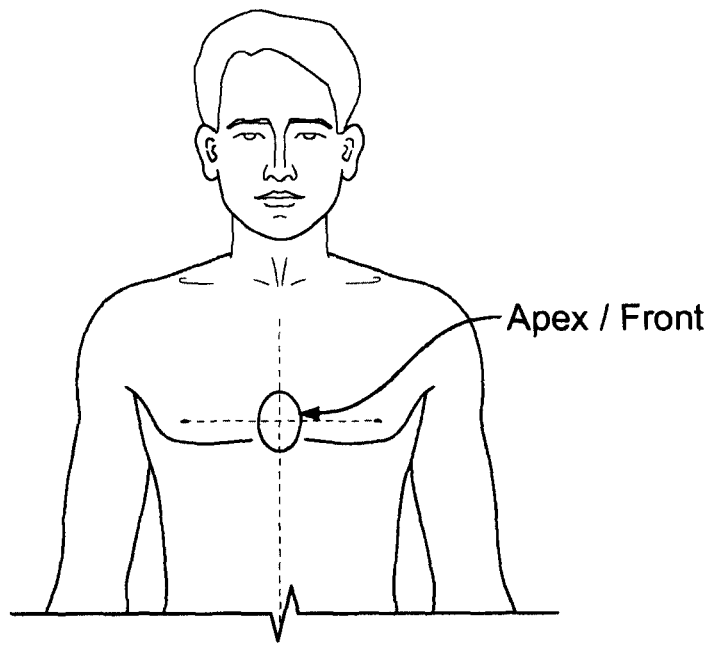
FIG. 21 is a plan view showing the triangular electrode of FIGS. 6-7 applied to a the chest of a patient.
Figure 22:
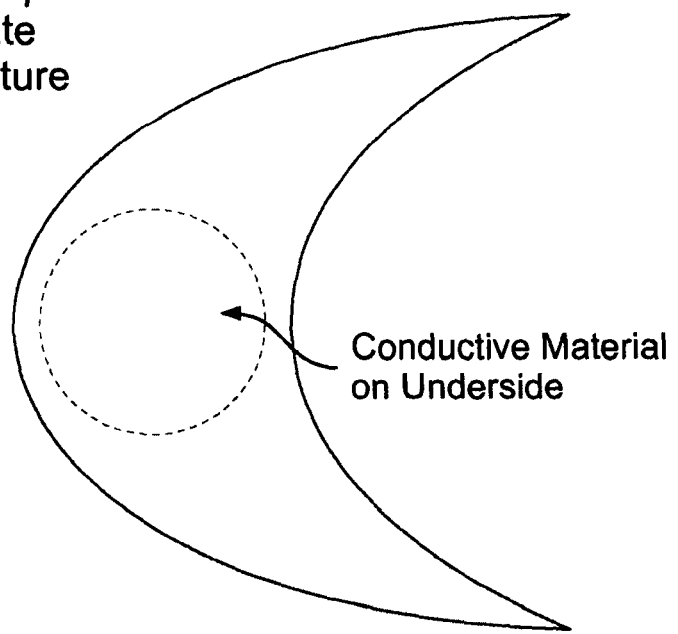
FIG. 22 is a plan view showing an alternative, crescent shaped electrode that could be used in place of the triangular electrode.

FIG. 21 shows the triangular electrode in place on the chest of the patient. The triangular shape greatly facilitates application of the electrode to the chest in the vicinity of a breast. The front electrode is adhered at the edge of the patient's breast, and the triangular shape has an advantage over circular or square electrodes in this location. These other shapes tend to fold or roll back on themselves. E.g., with a square electrode in this location, one corner of the electrode rides up on the breast, and will tend to roll back off the breast. This also tends to occur with circular electrodes. But with the triangular shape the problem is usually avoided. Another shape that will work well is a crescent shape, as shown in FIG. 22, with the smaller radius of the crescent closest to the breast. It is the lateral perimeter of the electrode that has the triangular or crescent shape.

Three ECG monitoring electrodes are built into the three corners of the electrode. Each monitoring electrode includes a solid gel layer 52 for contacting the patient, a conductive stud 54. (Ag/Cl) in contact with the gel layer, and conveying electrical potentials from the gel layer to the snap conductor 56 (Ni/Brass) to which a monitoring wire is connected. Alternatively, the snap conductor can be eliminated, and the ECG monitoring wires connected directly to the conductive studs 54.

The square defibrillation electrode 28 is shown in exploded, cross-sectional view in FIG. 8. It includes most of the same layers as the other defibrillation electrode (identified in the figure by using the same reference numeral for corresponding parts).

Figure 9:
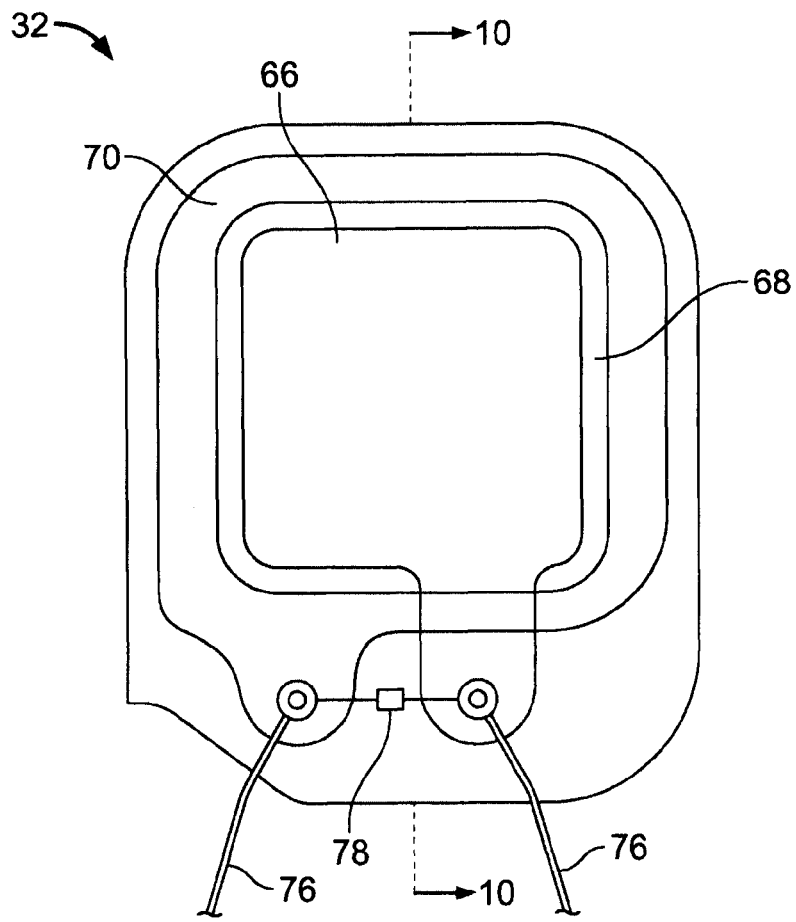
FIG. 9 is a plan view of the condition sensor (electrochemical cell) secured inside the electrode package.
Figure 10:
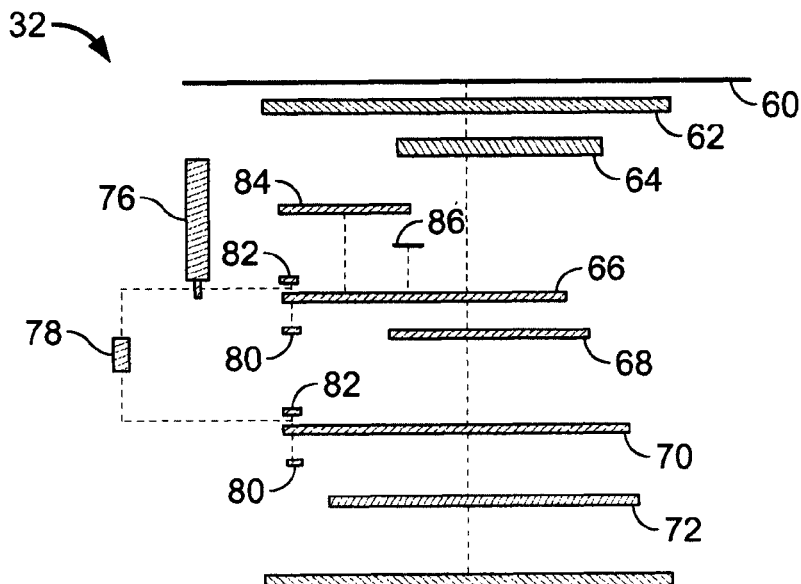
FIG. 10 is an exploded, cross-sectional view taken along section 10-10 in FIG. 9.

FIGS. 9-10 show the condition sensor 32, which functions as an electrochemical cell producing an electrical potential that is measured by the defibrillator to determine whether the moisture in the aqueous layer of the sensor has dried out. As the aqueous layer dries out (because moisture has escaped from the electrode package, e.g., because the package has been damaged), the potential of the electrochemical cell will fall off in magnitude. Once it falls below a threshold, indicating that the aqueous layer of the sensor has dried out, the defibrillator concludes that there is a high probability that the liquid-containing layers of the defibrillation electrodes have also dried out, and a warning prompt is delivered and the defibrillator may not deliver a defibrillation pulse to the electrodes.

Various other alternative tests could be applied to decide that the electrode is no longer suited for its intended use. E.g., the potential could be sampled frequently enough to establish a rate of change, and too high a rate of change could be a basis for deciding that something is wrong with the electrode. Depending on the circuitry used to measure the potential, a problem with the electrode could be detected by a voltage exceeding a threshold, and there could be multiple limits that the measured voltage is tested against.

FIG. 10 shows an exploded, cross-sectional view of the condition sensor. At the top of the stack of layers is a styrene release liner 60, which is removed when the sensor is installed in the electrode package, to expose adhesive on the vinyl mask layer 62, which is adhered to an interior surface of the electrode package to secure the condition sensor within the package. A aqueous layer 64 (gel) is positioned below the vinyl mask. A first metallic layer (metallic element) 66 (tin) is in contact with the gel. That is followed by an insulator layer 68 that is larger in area than the tin layer. Following the insulator layer is a second metallic layer (metallic element) 70 (aluminum) that is also in contact with the gel along its periphery outside of the extent of the insulator layer 68. A foam backing layer 72 and foam cover 74 complete the sandwich of layers. A wire 76 (electrical conductor) is connected to each of the metallic layers (both shown in FIG. 9; one shown in FIG. 10). A bridging resistor 78 (approximately 100K ohms) is connected across the two metallic layers to control the rate of the electrochemical reaction (the size of this resistor will vary with the metals and gels used in the electrochemical cell and with other factors well known to those skilled in the art). The wires 76 are connected to the metallic layers with rings 80 and sockets 82. A foam insulator layer 84 and length of tape 86 are positioned between the aqueous layer 64 and the first metallic layer 66.

Figure 11:
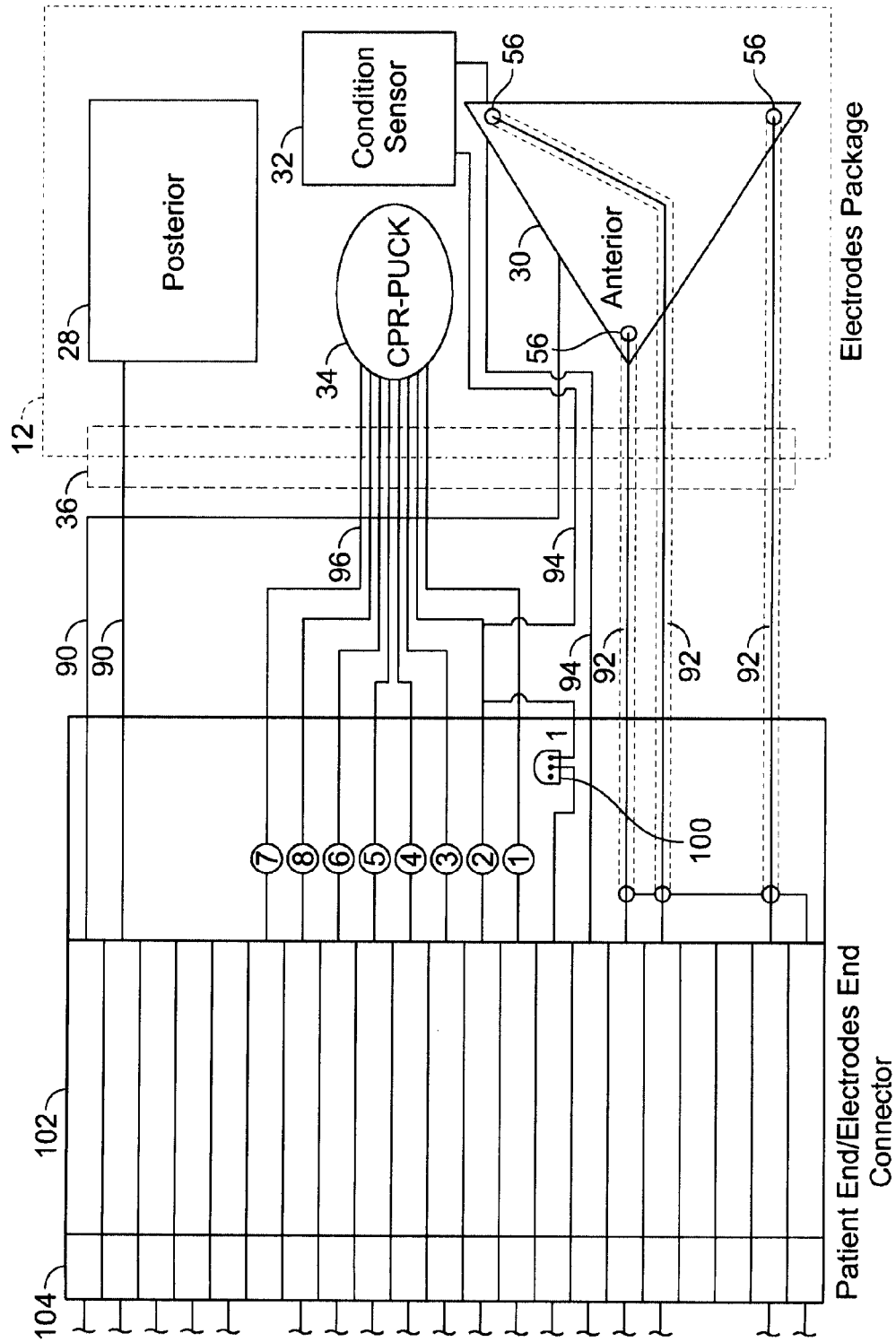
FIG. 11 is a schematic view of the electrical connections between the contents of the electrode package (electrodes, condition sensor, CPR puck) and the electrode package connector.
Figure 15:
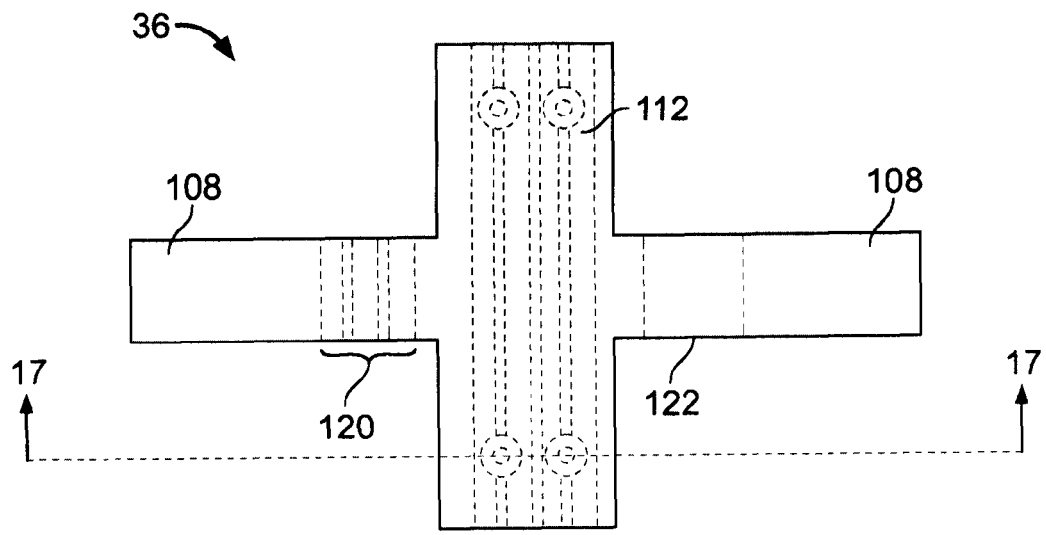
FIG. 15 is a plan view of the gasket element.
Figure 16:
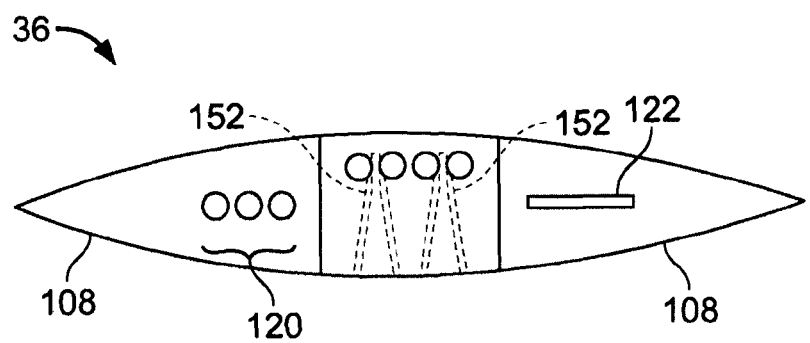
FIG. 16 is an end view of the gasket element.
Figure 17:
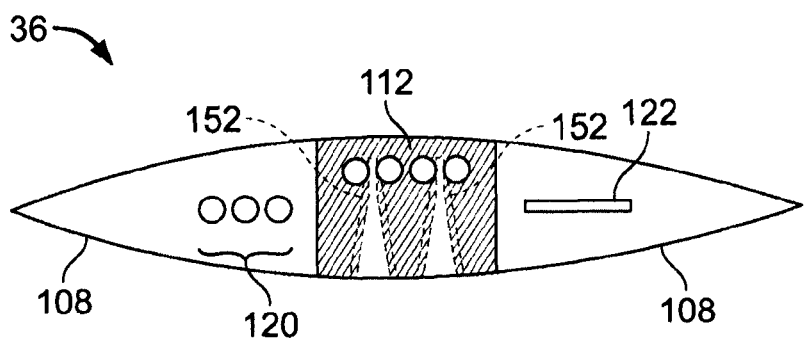
FIG. 17 is a cross-sectional view taken along section 17-17 in FIG. 15.
Figure 18:
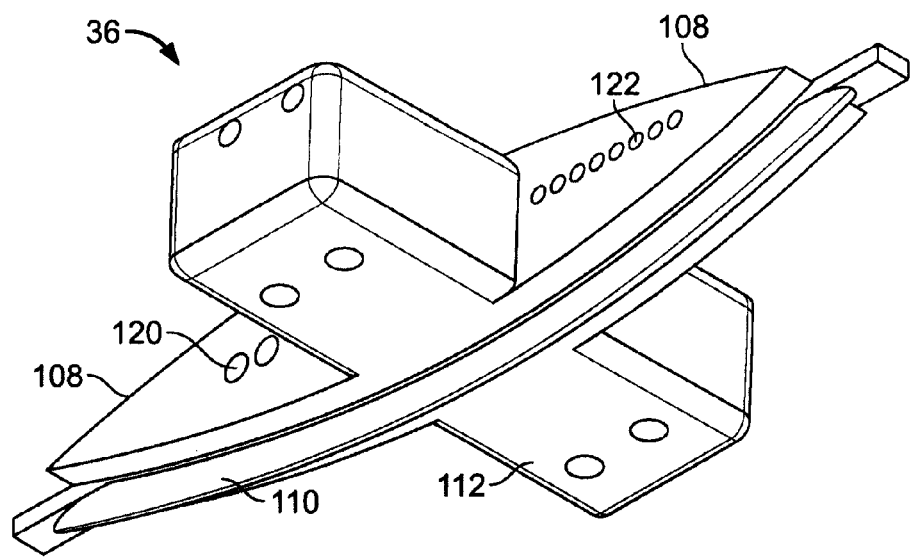
FIG. 18 is a perspective view of the gasket element.
Figure 19:
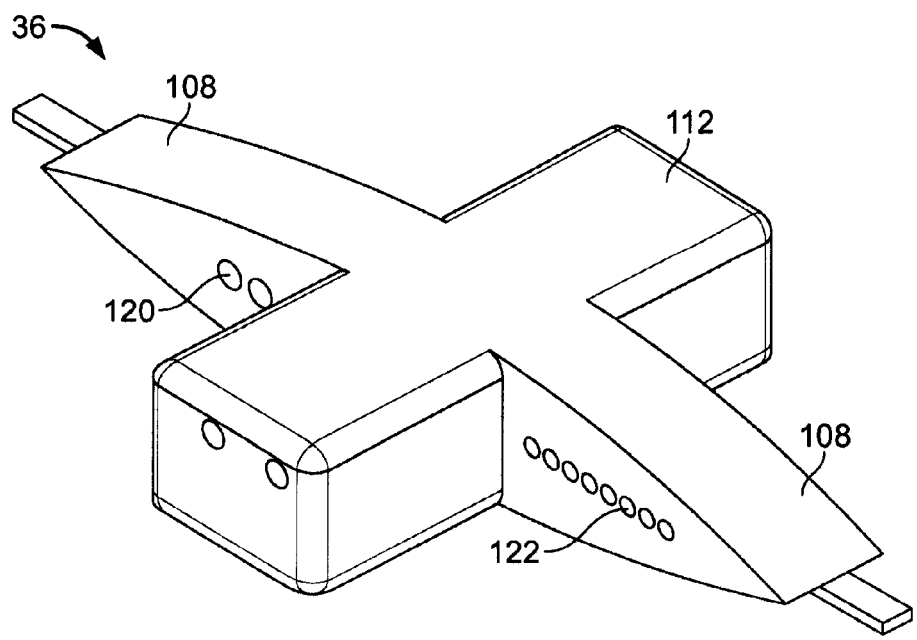
FIG. 19 is another perspective view of the gasket element.

FIG. 11 is an electrical schematic of the electrode package 12. Defibrillator electrodes 28, 30, condition sensor 32, and CPR puck 34 are shown within the electrode package. Cables connecting these elements tot the defibrillator pass out of the package through gasket element 36 (shown diagrammatically as a dashed rectangle in the schematic). Each defibrillation electrode has a single electrical conductor 90 configured to carry a high voltage signal. Three shielded wires 92 connect to the three ECG monitoring electrodes (designated by the snap conductors 56 at the locations of the monitoring electrodes). Two wires 94 connect to the condition sensor 32 (although in a preferred embodiment the electrical conductors connecting to the condition sensor are shared with other wires (e.g., one or more of the CPR puck wires). Eight wires 96 connect to the CPR puck.

All of wires 90, 92, 94, and 96 pass through the gasket element 36, and extend to an electrode package connector 102 (electrodes end connector), which is plugged into the patient end connector 104 of a cable that runs back to the defibrillator. The two connectors 102, 104 are shown mated in FIG. 11.

An electronic memory device 100 (e.g., a Dallas Maxim semiconductor chip, Part No. DS2431) is built into connector 102. A variety of information is stored on the chip, including: an authentication code, a configuration code (e.g., whether the package contains ECG monitoring electrodes, a CPR puck, or only defibrillation electrodes), the type of electrodes (adult or pediatric), the expiration date of the electrode package, the serial number, and the date of manufacturing and manufacturing line. Other information (or less information) could be stored on the chip.

FIGS. 12-19 show the gasket element through which the electrical conductors extend. The gasket element is shown in perspective view in FIGS. 18 and 19. It has gradually tapered extensions 108 extending in the direction in which it is adhered to the perimeter of the seal between the rigid base 20 and removable lid 16 of the package 12. A bead 110 of silicone adhesive seals one surface of the gasket element to the rigid base 20 of the package. This material is chosen so that the gasket will part from the rigid base when the electrodes are removed from the base. Between the tapered extensions 108 is a central portion 112.

The gasket element has at least one surface exposed to the interior of the electrode package and at least one surface exposed to the exterior of the package. Holes pass through the gasket element from a surface exposed to the interior to a surface exposed to the exterior. Three electrical paths for the monitoring electrodes pass through three holes 120. Eight smaller holes 122 (or one narrow opening) provide access for the electrical paths connecting the CPR puck.

When the gasket releases from the rigid base of the electrode package, certain electrical connections can be broken. For example, a conductive shorting element 130 that shorts across the two high-voltage defibrillation wires 90 (to allow testing of the integrity of these electrical pathways outside of the electrical package) is broken away. A second electrical connection that is broken is the connection to the condition sensor. Wires 94 (or their equivalent) that provide electrical pathways to the metallic layers of the condition sensor are disconnected from the condition sensor. This is necessary because the condition sensor in this implementation remains in the electrode package, as its usefulness as a package condition sensor has ended with the opening of the package.

Various techniques could be used to accomplish the disconnection of these electrical connections when the gasket element is removed. In the implementation shown herein, conductive posts 150, extending upward from the rigid base of the package, and normally received in conductive apertures 152 (conically shaped to receive the posts) in the gasket element, withdraw from the apertures when the gasket is removed the conductive posts shown are simply the ends of wires, bent 90 degrees to point upwardly, and stripped of insulation (the wider portion of the posts in the drawing is the wire with insulation; the narrower portion of the posts is the wire stripped of insulation). The conductive apertures (into which the posts extend) can be made from plated brass alloy with multiple fingers to engage the posts.

Figure 20:
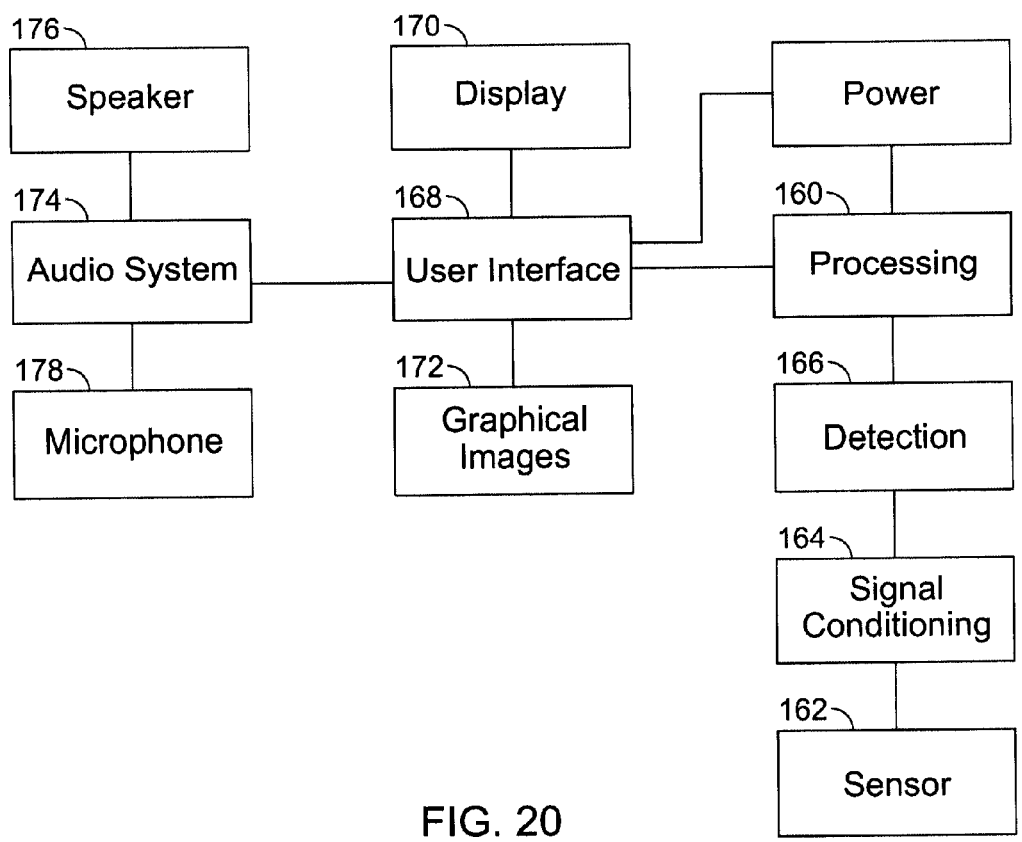
FIG. 20 is a block diagram of the electronics and components of the defibrillator of FIG. 1.

A general block diagram of the defibrillator is shown in FIG. 20. Processing circuitry and associated software (processing 160) is at the heart of the defibrillator. Inputs from sensors 162 such as the accelerometer in the CPR puck and the ECG monitoring electrodes on one of the electrode assemblies are received through signal conditioning and detection circuitry 164, 166. A user interface 168 provides outputs to a display 170 (and possibly to lights that direct the user to graphical images 172) and to an audio system 174 with speaker 176 and microphone 178.

Many other implementations other than those described above are within the invention, which is defined by the following claims. As mentioned earlier, it is not possible to describe here all possible implementations of the invention, but a few possibilities not mentioned above include the following: The condition sensor can also be used to determine whether a liquid-containing element of other types of medical devices has dried out or lost sufficient liquid that is not likely to be suited to work properly. For example, the sensor could be provided in the packaging for conductive pads used with defibrillation paddles, or with moist pads used for ultrasonic imaging.

Not all of the features described above and appearing in some of the claims below are necessary to practicing the invention. Only the features recited in a particular claim are required for practicing the invention described in that claim. Features have been intentionally left out of claims in order to describe the invention at a breadth consistent with the inventors' contribution.

What is claimed is:

1. A package in which a medical device is stored, the package comprising
    an outer shell providing a vapor barrier between an interior space inside the outer shell and an exterior environment;
    a medical device positioned in the interior space inside the outer shell;
    the medical device including a liquid-containing element that is subject to drying out as liquid from the liquid-containing element vaporizes and travels from the interior space to the external environment;
    a condition sensor comprising two metallic elements,
        each of the two metallic elements being composed of different metals, with each of the different metals selected so that the two metallic elements form an anode and a cathode of an electrochemical cell,
        each of the two metallic elements being in electrical contact with a conductive water-containing element, so that the water-containing element forms the electrolyte of the electrochemical cell, and
        an electrically conductive path extending from each of the metallic elements to a location wherein the electrochemical potential formed between the metallic elements can be measured to provide an indication of the degree to which the conductive water-containing element has dried out,
    wherein the medical device stored in the package further comprises at least one electrode, and wherein the electrode includes a metallic layer in electrical contact with a conductive liquid-containing layer through which electrical current is delivered to a patient when the electrode has been applied to a patient, the conductive liquid-containing layer being subject to drying out as liquid from the liquid-containing layer vaporizes and travels from the interior space to the external environment, and
    wherein the two metallic elements and water-containing element of the condition sensor are separate from and not shared with the liquid containing element and electrode of the medical device, and
    wherein the condition sensor provides an indication of whether the liquid-containing element of the medical device has dried out sufficiently that the electrode of the medical device should not be used.

2. The package of claim 1 wherein the electrode comprises a defibrillation electrode.

3. The package of claim 2 wherein the conductive liquid-containing layer of the electrode contains water and comprises an aqueous gel.

4. The package of claim 3 wherein the aqueous gel comprises a solid gel.

5. The package of claim 3 wherein the aqueous gel comprises a liquid gel.

6. The package of claim 3 wherein the water-containing element of the condition sensor comprises an aqueous gel layer.

7. The package of claim 6 wherein the metallic elements of the condition sensor are thin metallic layers and the aqueous gel is a thin gel layer in contact with each of the metallic layers.

8. The package of claim 7 wherein the thin gel layer is a different layer from the conductive liquid-containing layer of the defibrillation electrode.

9. The package of claim 2 wherein the condition sensor is configured so as to be retained in the package when the defibrillation electrode has been removed from the package.

10. The package of claim 2 wherein the electrically conductive paths extending from each of the metallic elements comprise electrical wires extending from the metallic elements at least to the outer shell.

11. The package of claim 10 further comprising a gasket element at the perimeter of the outer shell, the gasket element shaped and positioned so that one surface of the gasket element is exposed to the interior space within the outer shell and another surface of the gasket element is exposed to the exterior environment, the electrically conductive paths from the metallic elements of the condition sensor extending through the gasket element from the interior space to the exterior environment.

12. The package of claim 11 wherein the gasket element is configured so that when the package is opened and the defibrillation electrode applied to the patient, the gasket element is removed from the package causing the electrically conductive paths connected to the further electrical element to be broken.

13. The package of claim 2 wherein the electrochemical potential is measured inside the package and communicated to the exterior of the package.

14. The package of claim 2 wherein the condition sensor further comprises a resistive element electrically connected between the two metallic elements.

15. The package of claim 14 wherein the resistance of the resistive element is variable.

16. The package of claim 2 wherein the metals used in the metallic elements of the condition sensor include at least one metal that is the same as the metal used in the defibrillation electrode.

* * * * *

UNITED STATES PATENT AND TRADEMARK OFFICE
CERTIFICATE OF CORRECTION

| | |
|---|---|
| PATENT NO. | : 8,577,462 B2 |
| APPLICATION NO. | : 11/481245 |
| DATED | : November 5, 2013 |
| INVENTOR(S) | : Michael R. Dupelle et al. |

It is certified that error appears in the above-identified patent and that said Letters Patent is hereby corrected as shown below:

Title page, (57) Abstract, line 12, after "indication", insert -- whether --.

Signed and Sealed this
Twenty-fifth Day of February, 2014

Michelle K. Lee
*Deputy Director of the United States Patent and Trademark Office*